United States Patent [19]

Haynes

[11] 4,279,925

[45] Jul. 21, 1981

[54] N-PHENETHYLAMINOPROPIOPHENONES AS LIPOGENESIS INHIBITORS

[75] Inventor: George R. Haynes, Houston, Tex.

[73] Assignee: Shell Oil Company, Houston, Tex.

[21] Appl. No.: 170,347

[22] Filed: Jul. 21, 1980

Related U.S. Application Data

[62] Division of Ser. No. 115,467, Jan. 25, 1980.

[51] Int. Cl.$^3$ .................. A61K 31/22; A61K 31/275; A61K 31/165
[52] U.S. Cl. .................................. 424/311; 424/304; 424/324
[58] Field of Search ........................................ 424/311

[56] References Cited

U.S. PATENT DOCUMENTS

| | | | |
|---|---|---|---|
| 3,225,095 | 12/1965 | Thiele | 564/342 |
| 3,644,525 | 2/1972 | Thiele | 424/330 X |
| 3,829,469 | 8/1974 | Thiele et al. | 424/330 |

FOREIGN PATENT DOCUMENTS

| | | |
|---|---|---|
| 1815618 | 6/1971 | Fed. Rep. of Germany . |
| 1332930 | 10/1973 | United Kingdom . |

*Primary Examiner*—Frank Cacciapaglia, Jr.

[57] ABSTRACT

Certain N-phenethylaminopropiophenones inhibit lipogenesis in mammals.

1 Claim, No Drawings

N-PHENETHYLAMINOPROPIOPHENONES AS LIPOGENESIS INHIBITORS

This is a division, of application Ser. No. 115,467, filed Jan. 25, 1980.

DESCRIPTION OF THE INVENTION

It has been found that lipogenesis in mammals is inhibited by certain N-phenethylaminopropiophenones, described by the formula:

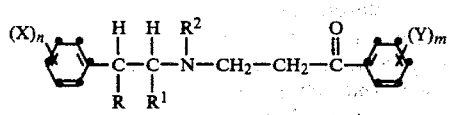

wherein
R is hydrogen or hydroxyl;
$R^1$ is hydrogen or methyl;
$R^2$ is hydrogen or methyl;
n is zero, one or two;
X is hydroxyl, with the proviso that when n is one, the hydroxyl moiety is bonded to the carbon atom at the 4-position in the phenyl ring, and when n is two, the hydroxyl moieties are bonded to the carbon atoms in the 3- and 4-positions of the phenyl ring;
m is zero or one;
Y is one of
nitro;
cyano;
hydroxyl;
alkyl;
alkoxy;
alkylthio;
alkanoyloxy;
alkenoyloxy;
alkanoylamino;
alkenoylamino;
alkoxycarbonylamino;
alkenyloxycarbonylamino;
3-(dialkylamino)alkyleneoxy;
2-(dialkenylamino)alkyleneoxy,
and their pharmacologically acceptable acid addition salts.

In these compounds, each alkyl moiety contains from one to six carbon atoms, each alkenyl moiety contains from three to six carbon atoms, and each type of moiety is straight-chain or branched-chain in configuration, while each alkylene moiety is ethylene, or ethylene substituted by methyl on the carbon atom bonded to the nitrogen atom of the aminoalkyleneoxy moiety.

Suitable salts are those of such acids as acetic, succinic, maleic, fumaric, propionic, citric, lactic, pamoic, hydrochloric, hydrobromic, sulfuric and phosphoric acids.

Compounds of Formula I that contain a chiral center are usually obtained as the racemic mixtures. Such mixtures can be resolved by known techniques. The isomers may have different activities as lipogenesis inhibitors. This invention contemplates all of the active isomers, as well as mixtures thereof.

The compounds of Formula I are known, being disclosed in U.S. Pat. Nos. 3,225,095, 3,644,525, 3,829,469; British Pat. No. 1,332,930, and German Pat. No. 1,815,618.

Compounds of Formula I have been found to inhibit lipogenesis in tissues of mammals. The manner in which they cause this effect is not known with certainty; it is believed that they interfere with the synthesis of fatty acids in the tissues. Their effectiveness for this purpose has been ascertained by immersing samples of swine adipose tissue in a liquid medium containing radioactive glucose and the test chemical, for a period of time, then isolating the lipid from the treated tissue and determining the incorporation of the radioactive carbon into lipid by means of scintillation counting techniques. These tests were conducted in swine adipose tissue because in swine, the primary site of lipogenesis—i.e., fatty acid synthesis—appears to be adipose tissue.

Described in more detail, the tests were conducted according to the following general procedure:

150 milligrams of slices of swine adipose tissue were incubated at 37° C. for 2 hours with shaking in 3 milliliters of Krebs-Ringer bicarbonate solution containing one-half the normal calcium ion concentration, 60 micromoles of glucose, 0.5 micro-Curie of glucose-$U^{14}C$, and 300 microunits of insulin, and 5% dimethyl sulfoxide (DMSO). The test compounds were added as suspensions or solutions in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1 v/v). The extracts were washed according to Folch et al. (J. Biol. Chem., 226, 497-509, (1957)), air-dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound in each case.

The following individual species of Formula I were tested:

| Compound No. | Where Known | Name |
|---|---|---|
| 1 | G.B. 1,332,930 | N-(3-(3-(2-hydroxy-2-(4-hydroxyphenyl)-1-methylethylamino)-1-oxopropyl)phenyl)-3-methyl-2-butenamide, hydrochloride. |
| 2 | G.B. 1,332,930 | (4-(3-(2-hydroxy-2-(4-hydroxyphenyl)-1-methylethylamino)-1-oxopropyl)phenyl)carbamic acid, ethyl ester, hydrochloride. |
| 3 | G.B. 1,332,930 | 3-methyl-3-(3-(2-hydroxy-2-(4-hydroxyphenyl)-1-methylethylamino)-1-oxopropyl)-2-butenoic acid, phenyl ester, hydrochloride. |
| 4 | Germany 1,815,618 | 3-(2-hydroxy-2-(4-hydroxyphenyl)-1-methylethylamino)-1-(3-propoxyphenyl)-1-propanone, hydrochloride. |
| 5 | Germany 1,815,618 | 3-(3-(2-hydroxy-2-(4-hydroxyphenyl)-1-methylethylamino)-1-oxopropyl)-benzonitrile, hydrochloride. |
| 6 | Germany 1,815,618 | 1-(3-ethoxyphenyl)-3-(2-hydroxy-2-(4-hydroxyphenyl)-1-methylethylamino)-1-propanone, hydrochloride. |
| 7 | Germany 1,815,618 | 3-(2-hydroxy-2-(4-hydroxyphenyl)-1-methylethylamino)-1-(3-(1-methylethoxy)phenyl-1-propanone, hydrochloride. |

-continued

| Compound No. | Where Known | Name |
|---|---|---|
| 8 | U.S. Pat. No. 3,644,525 | 3-(2-hydroxy-2-(4-hydroxyphenyl)-propylamino)-1-(3-nitrophenyl)-1-propanone, hydrochloride. |
| 9 | U.S. Pat. No. 3,644,525 | 3-(2-(3,4-dihydroxyphenyl)-2-hydroxyethylamino)-1-(4-methoxyphenyl)-1-propanone, hydrochloride. |
| 10 | U.S. Pat. No. 3,644,525 | 3-(2-(3,4-dihydroxyphenyl)-2-hydroxyethylamino)-1-(2-hydroxyphenyl)-1-propanone, hydrochloride. |
| 11 | U.S. Pat. No. 3,644,525 | 3-((2-hydroxy-2-(4-hydroxyphenyl)-ethyl)methylamino)-1-phenyl-1-propanone, hydrochloride. |
| 12 | U.S. Pat. No. 3,644,525 | 3-(2-(3,4-dihydroxyphenyl)-2-hydroxyethylamino)-1-phenyl-1-propanone, hydrochloride. |
| 13 | U.S. Pat. No. 3,829,469 | 1-(4-(2-(di-2-propenylamino)ethoxy)-phenyl)-3-(2-hydroxy-2-(4-hydroxyphenyl)-1-methylethylamino)-1-propanone, dihydrochloride. |
| 14 | U.S. Pat. No. 3,829,469 | 1-(4-(3-(dimethylamino)-2-methylpropoxy)phenyl)-3-(2-hydroxy-2-(4-hydroxyphenyl)-1-methylethylamino)-1-propanone, dihydrochloride. |
| 15 | U.S. Pat. No. 3,225,095 | (R-(R*,S*))-3-((2-hydroxy-1-methyl-2-phenylethyl)amino)-1-(3-methoxyphenyl)-1-propanone, hydrochloride. |

The data obtained from the tests are set out in Table 1, as the percent inhibition of lipogenesis compared to the results obtained in the control tests wherein only the test compound was omitted.

TABLE 1

| Compound No. | Percent Inhibition |
|---|---|
| 1 | 99 |
| 2 | 97 |
| 3 | 92 |
| 4 | 92 |
| 5 | 100 |
| 6 | 89 |
| 7 | 94 |
| 8 | 100 |
| 9 | 88 |
| 10 | 97 |
| 11 | 100 |
| 12 | 97 |
| 13 | 82 |
| 14 | 96 |
| 15 | 100 |

The ketones of Formula I can be used to control lipogenesis in warm-blooded animals such as, for example, pets, animals in a zoo, livestock, fur-bearing animals and domestic animals, including but not limited to dogs, cats, mink, sheep, goats, swine, cattle, horses, mules and donkeys. The effect is obtained by administering an effective amount of one or a mixture of two or more of the ketones orally or parenterally to the animal. They may be administered as such, or as an active ingredient of a conventional pharmaceutical formulation. They may be administered orally by any convenient means. Thus, they may be orally administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups and elixirs. For parental administration, they may be in the form of a solution, suspension, dispersion or emulsion. They can be administered in the form of an implant or other controlled sustained release formulation. Inert carriers, such as one or more of water, edible oil, gelatin, lactose, starch, magnesium sterate, talc or vegetable gum can be used. The dosage of the ketone needed to inhibit lipogenesis will depend upon the particular ketone used, and the particular animal being treated. However, in general, satisfactory results are obtained when the ketone are administered in a dosage of from about 1 to about 400 milligrams per kilogram of the animal's body weight. The ketone can be administered in a single dose or in a series of doses in the same day, or over a period of days. For any particular animal, a specific dosage regimen should adjusted according to the individual need, the particular ketone(s) used as the inhibitor, and the professional judgment of the person administering or supervising the administration of the inhibitor. It is to be understood that the dosages set forth herein are exemplary only, and that they do not, to any extent, limit the scope or practice of the invention.

What is claimed:

1. A method of inhibiting lipogenesis in a mammal, which comprises administering, to a mammal in need of such treatment, orally or parenterally a lipogenesis inhibiting amount of a compound of the formula:

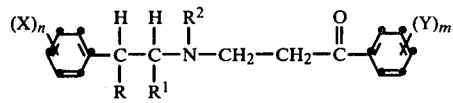

wherein
R is hydrogen or hydroxyl;
$R^1$ is hydrogen or methyl;
$R^2$ is hydrogen or methyl;
n is zero, one or two;
X is hydroxyl, with the proviso that when n is one, the hydroxyl moiety is bonded to the carbon atom at the 4-position in the phenyl ring, and when n is two, the hydroxyl moieties are bonded to the carbon atoms in the 3- and 4-positions of the phenyl ring;
m is one;
Y is alkanoyloxy or alkenoyloxy,
and their pharmacologically acceptable acid addition salts.

* * * * *